United States Patent
Steinsapir

(10) Patent No.: US 7,846,457 B2
(45) Date of Patent: Dec. 7, 2010

(54) COSMETIC USE OF BOTULINUM TOXIN FOR THE TREATMENT OF EYEBROW AND FOREHEAD PTOSIS, AND UNWANTED EYEBROW EXPRESSION

(76) Inventor: Kenneth D. Steinsapir, 11645 Wilshire Blvd., Suite 750, Los Angeles, CA (US) 90025

(*) Notice: Subject to any disclaimer, the term of this patent is extended or adjusted under 35 U.S.C. 154(b) by 493 days.

(21) Appl. No.: 11/429,057

(22) Filed: May 4, 2006

(65) Prior Publication Data

US 2007/0259001 A1    Nov. 8, 2007

(51) Int. Cl.
| | | |
|---|---|---|
| A61K 39/08 | (2006.01) | |
| A61K 39/02 | (2006.01) | |
| A61K 39/00 | (2006.01) | |
| A61K 38/00 | (2006.01) | |

(52) U.S. Cl. ............... 424/247.1; 424/236.1; 424/239.1; 424/184.1; 530/300

(58) Field of Classification Search ........................ None
See application file for complete search history.

(56) References Cited

U.S. PATENT DOCUMENTS

| | | | |
|---|---|---|---|
| 5,401,243 | A | 3/1995 | Borodic |
| 6,358,917 | B1 | 3/2002 | Carruthers et al. |
| 6,861,058 | B2 | 3/2005 | Aoki et al. |
| 2005/0208075 | A1 | 9/2005 | Borodic |

OTHER PUBLICATIONS

Ahn et al (Plastic and Reconstructive Surgery, Mar. 2000, p. 1129-1135).*
Huilgol et al (Dematol Surg, 25:5 May 1999, p. 373-376).*
Heckmann et al (J. Am Acad Dermatol, Published online May 23, 2001, p. 1-7).*
A. Scott, A. Rosenbaum, C. Collins (1973) Pharmacologic Weakening of Extraocular Muscles; Invest Ophthalmol. 12:924-7.
P. Savino and M. Maus (1991) Botulinum Toxin Therapy; Neurol. Clin. 9:205-24.
J. Melling, P. Hambleton, C. Shone. (1988) *Clostridium botulinum* Toxins: Nature and Preparation for Clinical Use; Eye 2: 16-23.
J. Carruthers and A. Carruthers (1992) Treatment of Glabellar Frown Lines With *C. botulinum*-A Exotoxin; J. Dermatol. Surg. Oncol. 18:17-21.
J. Carruthers and A. Carruthers (2004) Botox: Beyond Wrinkles; Clin. Dermatol. 22:89-93.
A. Karacalar, A. Korkmaz, A. Kale, and C. Kopuz (2005) Compensatory Brow Asymmetry: Anatomic Study and Clinical Experience; Aesthetic Plast. Surg 29: 119-23.
W. Huang, A. Rogachefsky, and J. Foster (2000) Browlift With Botulinum Toxin; Dermatol. Surg. 26:55-60.
S. Teske, et. al. (1998) Hering's Law and Eyebrow Position; Ophthal. Plast. Reconstr. Surg. 14: 105-6.
A. Trindade De Alemeida and S. Cernea (2001) Regarding Browlift With Botulinum Toxin; Dermatol. Surg. 27:848-849.
E. Schantz, D. Kautter (1978) Standardized Assay for *Clostridium botulinum* Toxins. J Assoc Anal Chem 61:96-99.
S. Huilgol, A. Carruthers, and J. Carruthers (1999) R Ing Eyebrows With Botulinum Toxin; Dermatol. Surg. 1999: 373-5.
D. Knize (1996) An Anatomically Based Study of the Mechanism of Eyebrow Ptosis; Plastic & Reconstructive Surgery, 97:1-19.
R. Bhidayasiri, D. Truong (2005) Expanding Use of Botulinum Toxin; Journal of Neurological Sciences 235:1-9.
A. Chen, A. Frankel (2003) Altering Brow Contour With Botulinum Toxin; Facial Plastic Surgery Clinics of North America 11:457-464.

* cited by examiner

*Primary Examiner*—Vanessa L. Ford
(74) *Attorney, Agent, or Firm*—Lawrence N. Ginsberg

(57) ABSTRACT

A method of temporarily elevating the eyebrow position and softening undesirable glabellar muscle activity to affect a more desirable appearance. In a broad aspect the invention comprises injecting small quantities of *botulinum* toxin (BTX) equivalent in activity to 0.001 to 1.0 Units of *botulinum* toxin A, dissolved in 10 to 50 microliters microdroplets of injectable saline carrier, and injected 0.5 to 1.0 millimeters below the skin surface to treat the septal and orbital orbicularis oculi muscles, on each side of a patient's face. In sufficient numbers, injected microdroplets of BTX are able to selectively weaken these muscles. This method preferably also includes using microdroplets of BTX to treat: a) the depressor supercilii muscle, on each side; b) the procerus muscle; c) the corrugator supercilii muscle, on each side; and d) the inferior limit of the frontalis muscle where it meets the superior aspect of the orbital portion of the orbicularis oculi muscle.

12 Claims, 2 Drawing Sheets

FIG. 2
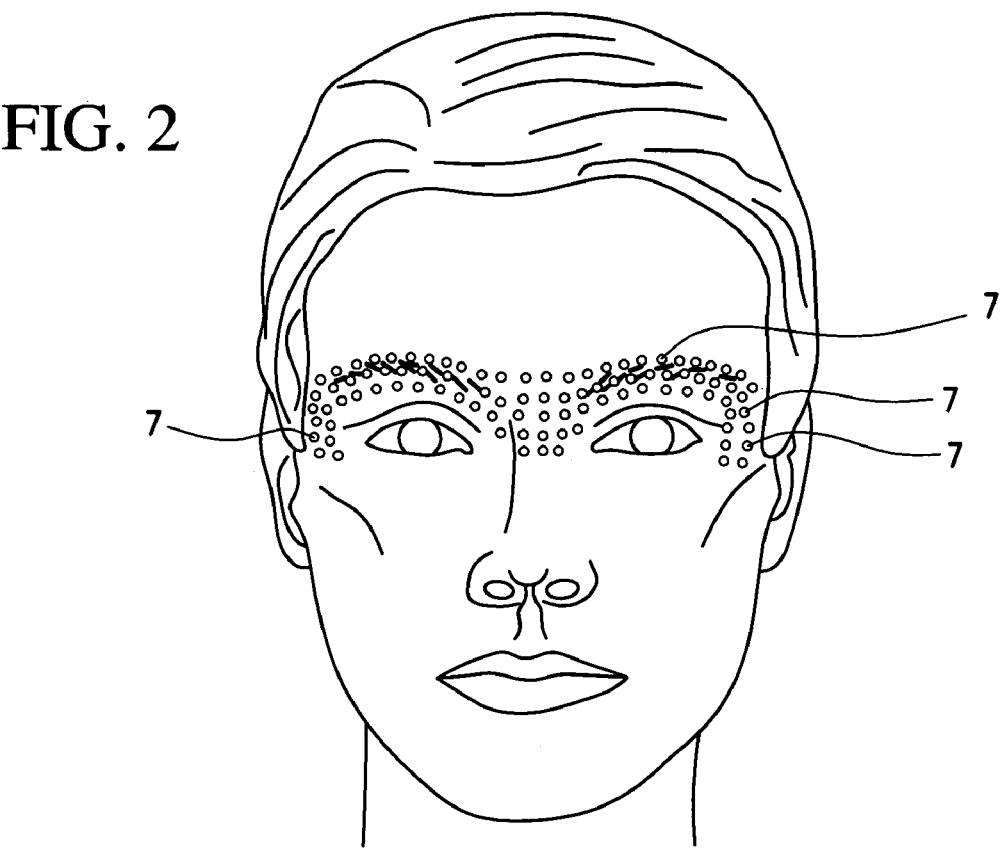
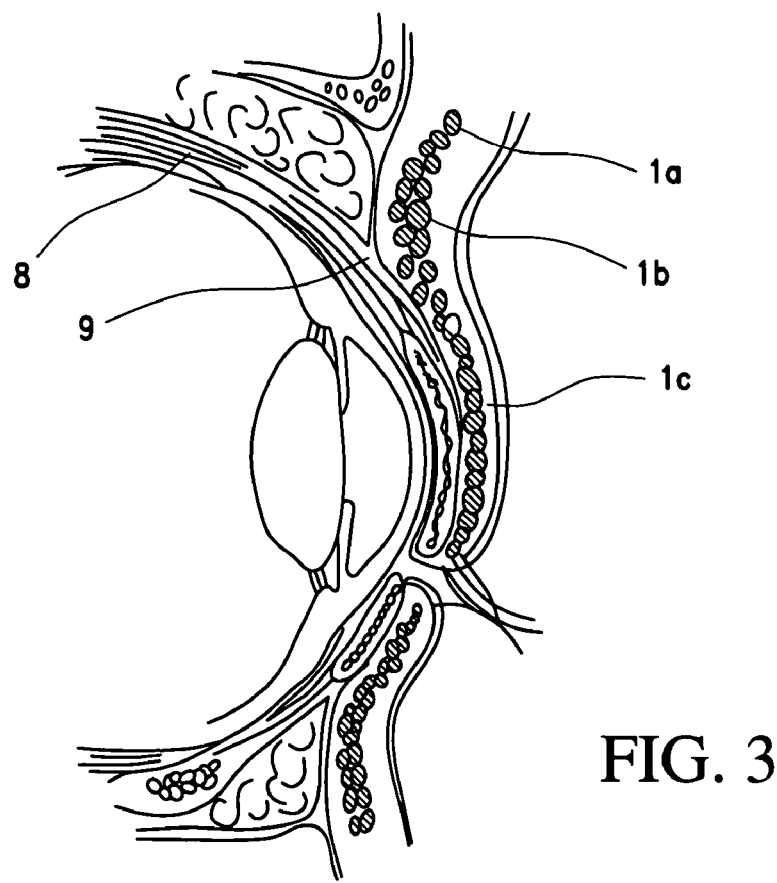
FIG. 3

COSMETIC USE OF BOTULINUM TOXIN FOR THE TREATMENT OF EYEBROW AND FOREHEAD PTOSIS, AND UNWANTED EYEBROW EXPRESSION

BACKGROUND OF THE INVENTION

1. Field of the Invention

The present invention relates generally to the cosmetic use of neurotoxin agents and more particularly to an improved method for injecting botulinum toxin (BTX).

2. Description of the Related Art

The position and appearance of the eyebrows is determined at rest and dynamically by the opposing action of several groups of muscles that act on the eyebrow. The frontalis muscle primarily performs eyebrow elevation. Brow elevation is opposed by the septal and orbital portions of the orbicularis oculi muscle, including the depressor supercilii component of the orbicularis oculi muscle, and the procerus muscle (D. Knize (1996) An anatomically based study of the mechanisms of eyebrow ptosis; Plast. Reconstr. Surg. 97:1321-33). The medial position of the eyebrow is also determined by the activity of the corrugator supercilii muscle. Additionally the shape of the brows is also determined by the activities of the eyebrow elevators and the eyebrow depressor muscles where they interdigitate along the eyebrow to create facial expression (A. Karacalar, et al (2005) Compensatory brow asymmetry: anatomic study and clinical experience; Aesthetic Plast. Surg 29: 119-23).

An aesthetically pleasing appearance is associated with relatively few lines in the forehead, no creasing between the eyebrows at the root of the nose, commonly known as the worry line, no lines across the bridge of the nose, and an absence of facial lines lateral to the eyes, commonly known as crow's feet. Additionally, with age there is a gradual fall in the position of the eyebrows creating hooding over the upper eyelids, which is known as brow ptosis. Aesthetically this change makes the eyes look small and is not desirable. Hooding of the upper eyelids by the descending eyebrow tissue results in a neural reflex that increases the activity of the frontalis muscle in an effort to keep the vision clear of the descending tissue that would otherwise obstruct vision or interfere with eyelid function (S. Teske, et. al. (1998) Hering's law and eyebrow position; Ophthal. Plast. Reconstr. Surg. 14: 105-6).

Botulinum toxin (BTX), which is produced by the bacterium Clostridium botulinum, inhibits the release of acetylcholine at the neuromuscular junction weakening muscle contraction. The degree of muscle paralysis will vary with the intensity of neuromuscluar blockade. Several immunologically distinct botulinum toxin serotypes have been identified including A, B, C, D, E, F, and G. They vary in the severity and duration of the neuromuscular blockade and, consequently, the severity of the paralysis they produce (J. Melling, et. al. (1988) Clostridium botulinum toxins: nature and preparation for clinical use; Eye 2: 16-23). The term BTX is the generic term for this family of neurotoxins. Botulinum toxin A (BTX-A) is currently available from two commercial sources: Allergan Inc., Irvine, California, under the trade name BOTOX®, and from Ipsen Ltd., Slough, UK under the trade names DYSPORT® and RELOXIN®. Botulinum toxin B (BTX-B) is available from Solstice Neurosciences, Inc, South San Francisco, Calif., under the trade name MYOBLOC®. The relative strengths of these products vary. For purposes of clarity, dose and dilutions in the following discussions will refer to the widely available botulinum toxin A product by Allergan Inc. (BOTOX®). The dose and dilution must be adjusted for the other commercially available botulinum products according to their relative strength.

The first clinical application of botulinum toxin was by Dr. Allan Scott for the treatment of strabismus and then for a form of localized eyelid dystonia known as blepharospasm (A. Scott, et. al. (1973) Pharmacologic weakening of extraocular muscles; Invest Ophthalmol. 12:924-7). These were the first clinical applications approved by the FDA for treatment with botulinum toxin A (P. Savino and M. Maus (1991) Botulinum toxin therapy; Neurol. Clin. 9:205-24). Clinical use of botulinum toxin A in the treatment of spastic facial disorders lead to the clinical observation that many of the treated patients had improvement in the deep glabellar furrows between the eyebrows (J. Carruthers and A. Carruthers (1992) Treatment of glabellar frown lines with C. botulinum-A exotoxin; J. Dermatol. Surg. Oncol. 18:17-21). Recently, FDA approval was granted for the cosmetic use of botulinum toxin A for the treatment of the worry line between the eyebrows. Other FDA indications for botulinum toxin A include treatment for cervical dystonia, a type of neck spasm, and axillary hyperhydrosis, also known as excessive armpit sweating (R. Bhidayasiri and D. Truong (2005) Expanding use of botulinum toxin; J. Neurol. Sci. 235:1-9).

Botulinum toxin A is clinically used more broadly than what is approved by the FDA. This wider usage is permissible for licensed physicians and is referred to as "off label" use (J. Carruthers and A. Carruthers (2004) Botox: beyond wrinkles; Clin. Dermatol. 22:89-93). Cosmetically, BTX is used to soften dimpling in the chin, relax the depressor anguli oris muscle that contributes to a turned down corners of the mouth as detailed by Carruthers in U.S. Pat. No. 6,358,917, and a range of locations and effects around the eyes and in the forehead. Previously, BTX has been used to elevate the eyebrow position by treating between the eyebrows and at the lateral eyebrow with relatively few injection sites (24) and with relatively large quantities of BTX (1.5-2.5 Units Botulinum toxin A) (W. Huang, et. al. (2000) Browlift with botulinum toxin; Dermatol. Surg. 26:55-60). This technique is limited by fear of inducing the undesired side effect of ptosis of the upper eyelid, where the upper eyelid droops causing visual obstruction. This can be caused by the unwanted diffusion of BTX into the eyelid affecting the levator palpebrae superioris muscle responsible for eyelid elevation (A. Trindade De Alemeida and S. Cernea (2001) Regarding browlift with botulinum toxin; Dermatol. Surg. 27:848-849).

As will be disclosed below, the present inventor has found that it is possible to treat the eyebrow depressors extensively yet avoid the unwanted side effects by using a microdroplet injection technique and trapping the injected BTX between the skin and the orbicularis oculi muscle, the most important eyebrow depressor.

SUMMARY OF THE INVENTION

The present invention is a method of temporarily elevating the eyebrow position and softening undesirable glabellar muscle activity to affect a more desirable appearance. In a broad aspect the invention comprises injecting small quantities of botulinum toxin (BTX) dissolved in microdroplets of injectable saline carrier to treat the septal and orbital orbicularis oculi muscles, on each side of a patient's face. In sufficient numbers, injected microdroplets of BTX are able to selectively weaken these muscles. This method preferably also includes using microdroplets of BTX to treat: a) the depressor supercilii muscle, on each side; b) the procerus muscle; c) the corrugator supercilii muscle, on each side; and d) the inferior limit of the frontalis muscle where it meets the superior aspect of the orbital portion of the orbicularis oculi muscle. As the term is used herein, a microdroplet is defined as 0.01 to 0.05 milliliters of injectable saline, which is used as an injectable carrier for a dissolved quantity of BTX, creating a BTX solution. The quantity of BTX dissolved in a microdroplet will vary with the BTX product chosen and the clinical effect desired. BTX is highly potent so that even with the highest doses of BTX used clinically, the solution comprising the microdroplet will be mostly water by weight and volume. While the quantity of BTX in a microdroplet may vary from 0.001 to 1.0 Units of *botulinum* toxin A (BOTOX®, Allergan Inc.), in the preferred embodiment, a microdroplet will typically contain 0.25 to 0.5 Units of *botulinum* toxin A. As noted above, microdroplets of other *botulinum* toxin products must be adjusted by the number of Units based on their relative strength.

The microdroplet injections are preferably placed approximately 0.5 to 1 millimeter below the skin surface to distribute the BTX between the skin and the underlying muscle to limit the diffusion of the BTX.

The present method alleviates or improves eyebrow ptosis. This method makes use of the fact that the orbital orbicularis oculi muscle inserts into the skin and therefore resides just below the dermis layer of the skin. Small quantities of BTX placed superficially by needle between the dermis and the orbicularis oculi muscle will tend to be trapped at the site of placement causing a more localized effect than larger quantities of BTX injected deep to the orbicularis oculi muscle. Limiting the volume and quantity of BTX injected into each site further reduces the risk of BTX diffusion.

As noted above, the microdroplet injection volume at each site is in a range between 0.01 to 0.05 ml. Each microdroplet of BTX injected contains 0.001 to 1.0 Units of *botulinum* toxin A adjusted based on the desired degree of muscle weakening. In the current preferred embodiment, the BTX solution is prepared so that each microdroplet contains 0.25 to 0.5 Units of *botulinum* toxin A. Typical total dosages of BTX-A administered during a treatment vary between 25-75 Units adjusted based on the muscle mass of the individual being treated and the desired degree of muscle weakening. The cumulative effect of these microdroplet injections of BTX is selective weakening of the eyebrow depressor effect of the orbicularis oculi muscle, including the depressor supercilli portion of this muscle. The microdroplet treatment also preferably includes the procerous muscle and the corragator muscle to weaken all of the muscles at the orbital rim that contribute to eyebrow depression.

The method of BTX administration of the present invention makes it possible to extensively treat the area below the eyebrow without unwanted side effects. Previous treatments methods avoided this area because they commonly produced a fall in the position of the eyelid with visual obstruction known as upper eyelid ptosis.

BRIEF DESCRIPTION OF THE DRAWINGS

FIG. 2 illustrates a typical periocular microdroplet BTX treatment, in accordance with the principles of the present invention, in which each individually injected microdroplet is depicted with a circle.

FIG. 3 is an illustration of the cross-section of the orbit that shows the relationship of the levator palbepra superioris muscle to the orbicularis oculi muscle.

DETAILED DESCRIPTION OF THE INVENTION

Figure 1:
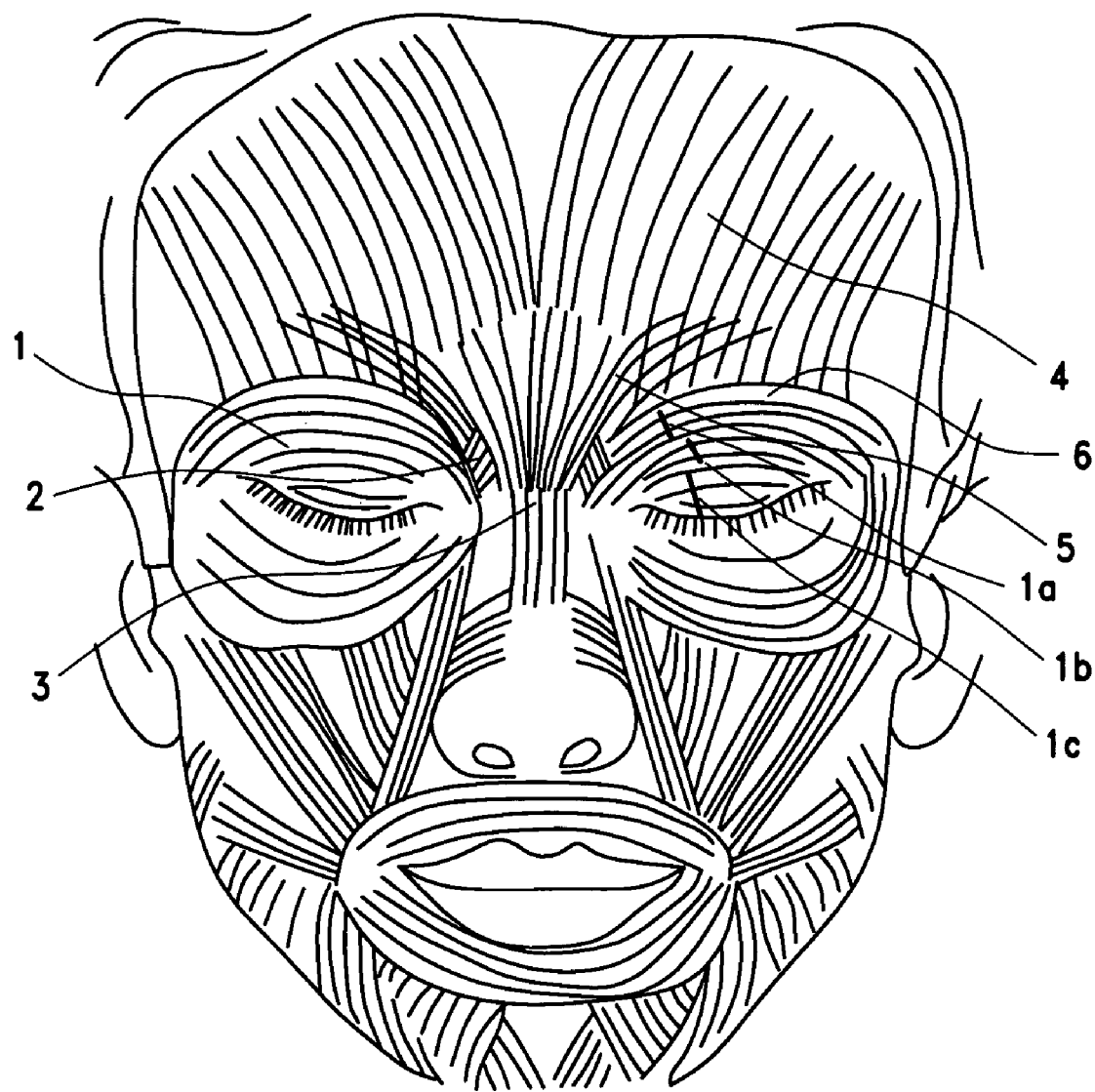
FIG. 1 is an illustration of the facial muscles showing the location of the muscles to be injected in accordance with the principles of the present invention.

*Botulinum* toxin is a general term for any of the neurotoxins produced by any of the members the bacterial organisms that belong to the *Clostridium botulinum* species. Fourteen pathogenic strains of this species have been isolated from *botulism* outbreaks in humans and animals. These organisms have been shown to produce seven immunologically distinct types of neurotoxin (types A,B,C,D,E,F, and G). The term "BTX" is used to refer to this family of neurotoxins. Currently only *botulinum* toxin types A and B are commercially available for clinical use: *Botulinum* toxin A from Allergan Inc., Irvine, Calif., under the trade name BOTOX®, and from Ipsen Ltd., Slough, UK, under the trade name DYSPORT® and RELOXIN®. *Botulinum* toxin B is available from Solstice Neurosciences, Inc, South San Francisco, Calif., under the trade name MYOBLOC®.

The treatment dose of BTX is measured in "Unit" equivalents, which is defined on the basis of a biological assay. One Unit equivalent is defined as the mean $LD_{50}$ (the dose that is lethal for 50% of the animals tested) for female Swiss Webster mice with a weight of 18-20 grams (Schantz EJ, Kaultner DA (1978) Standardized assay for *Clostridium botulinum* toxins. J Assoc Anal Chem 61:96-99. The estimated $LD_{50}$ for BOTOX® (*botulinum* toxin A) for a 70 kg adult human is 2800 Units (40 Units/kg). DYSPORT® is roughly ten times less potent than the BOTOX® product. The *Botulinum* toxin B product MYOBLOC® is 30 to 50 times less potent than the BOTOX® product. Consequently, the dose of these agents must be adjusted to achieve an equivalent treatment effect.

Commercially available BTX-A comes in a unit dose form that is reconstituted just prior to use. Currently the only BTX-A approved by the FDA is BOTOX® from Allergan Inc. This product is packaged in a 100 Unit vial as a sterile lyophilized powder stored at 8 degrees C. or less until use. The toxin is dissolved with unpreserved normal saline (sodium chloride 0.9% for injection) just prior to use to form a solution of a given dilution based on the volume of saline used to reconstitute the BTX-A. The manufacturer recommends that it be used within 4 hours after reconstitution to avoid loss of potency. The saline is introduced after breaking the vacuum present in the unit vial to avoid foaming of the solution, which may affect the potency.

The vial that the commercially available BTX products come in have a rubber stopper which permits the reconstituted solution to be drawn up without removing the rubber stopper that seals the vial. This stopper is cleaned with an alcohol wipe and allowed to dry. An 18-gauge needle on a tuberculin type syringe is used to draw up the desired volume of solution. In the case of BOTOX®, the concentration of the solution is determined by the quantity of saline used to reconstitute the BTX-A in the vial. For this method, typically 2 to 4 ml of unpreserved saline are used to reconstitute the lyophilized product. These volumes of dilution produce concentrations that vary from 25 Units to 50 Units per milliliter or 2.5 Units to 5 Units per 0.1 milliliter or 0.25 to 0.5 Units per 0.01 milliliter. Prior to treatment the 18-gauge needle is removed and replaced with a 30, 31 or 32 gauge needle with 8 to 13 mm length. The presently available BTX-B product comes as a solution containing 5000 Units per milliliter and can be diluted as needed.

Referring now to FIG. 1, an illustration of the facial muscles is shown, illustrating the location of the muscles to be injected and other surrounding muscles. The muscles to be injected include portions of the orbicularis oculi muscle, designated generally as 1, including the orbital portion 1*a* and the septal portion 1*b*. The tarsal portion 1*c* is generally avoided to prevent weakness of lid closure. Other muscles preferably injected include the depressor supercilli muscle 2, the procerous muscle 3, the frontalis muscle 4, the corragator supercilli muscle 5, and d) the inferior limit of the frontalis muscle where it meets the superior aspect of the orbital portion 1a of the orbicularis oculi muscle (as shown by numeral designation 6). Treatment of the frontalis muscle is strictly limited to the inferior portion on each side that interdigitates with the opposing orbital portion of the orbicularis oculi muscle. Interaction of these two muscle groups at this location is responsible for muscular pinching along the eyebrow, which is generally undesirable.

Patients are typically seated upright in a chair with a headrest to prevent movement. The skin is typically lightly anesthetized with a topical anesthetic or with ice. Next the skin is cleaned with alcohol and allowed to dry. A tuberculin syringe holds 1 milliliter of solution. The needle is inserted just below the dermis, which along the eyebrow is one millimeter below the skin surface. The goal is to place the medication between the skin and the muscle to be treated. A microdroplet of BTX is injected at each site. Each microdroplet contains 0.001 to 1.0 Units of *botulinum* toxin A (BOTOX®, Allergan Inc.) in 0.01 to 0.05 milliliters of injectable saline. In the preferred embodiment of the invention, the typical microdroplet will contain 0.25 to 0.5 Units of BTX-A. Very little diffusion of the BTX occurs when the medication is placed in this fashion.

FIG. 2 demonstrates a typical treatment pattern, with each individually injected micro-droplet depicted with a circle (circles being designated by numeral designations 7). Patients are advised not to massage the area or work out for 24 hours to further reduce the likelihood of dissipation of the toxin. The total dose of BTX-A may vary from 10 Units to 100 Units depending on the individual treatment plan. Most patients benefit from doses in the range of 30 to 60 Units. A total treatment may require between 30 and 100 treatment sites.

In contrast, prior described applications of BTX along the brow have made no attempt to keep the agent placed between the skin and the muscle and rely on larger aliquots of medication. (A. Chen and A. Frankel (2003) Altering brow contour with *botulinum* toxin; Facial Plast. Surg. Clin. North Am. 11: 457-64). Consequently, the injected BTX can diffuse creating unwanted side effects. In particular, injections below the eyebrow have been avoided because the risk of diffusion of the agent into the eyelid causing unwanted weakening of the levator palebebrae superioris, the muscle that raises the eyelid, producing an unwanted droop of the eyelid (S. Huilgol, A. Carruthers, and J. Carruthers (1999) Raising eyebrows with *botulinum* toxin; Dermatol. Surg. 1999: 373-5).

Referring to FIG. 3, the close proximity of the levator palebebrae superioris muscle 8 and its tendon 9 to the orbital 1a, septal 1b, and tarsal 1c portions of the orbicularis oculi muscle 1 can be appreciated. By placing low volume microdroplets of BTX with as little as 0.01 milliliters of volume just below the dermis, unwanted diffusion and side effects are avoided. This permits treatment of larger areas of the orbicularis oculi muscle in the upper eyelid and below the eyebrow which results in an elevation of the eyebrow tissue in a manner that is not possible with previously described techniques that specifically avoid treating this area. It is the use of microdroplets of BTX solution placed just below the skin surface that makes the treatment of this area possible. By weakening a much larger percentage of the orbicularis oculi muscle, the muscle primarily responsible for eyebrow depression, in the upper eyelid above the eyelid crease, in the sub-eyebrow area, at and just above the eyebrow, laterally in the crows feet area and along the medial aspect of the nose in this controlled manner, a profound forehead lift is possible. This degree of lift is not achievable with previously described methods without the risk of affecting the levator palebebrae superioris muscle deep in the eyelid that is responsible for elevating the upper eyelid. When diffusion of BTX deep into the eyelid occurs, partial or complete paralysis of the upper eyelid can occur preventing the opening of the eyelid. This undesired effect while temporary is unacceptable to those being treated.

The microdroplet method can also be used to treat the depressor supercilli, procerus muscle and the corrugators, which also contribute to brow depression in the center of the brow region over the root of the nose.

Other embodiments and configurations may be devised without departing from the spirit of the invention and the scope of the appended claims.

The invention claimed is:

1. A method of temporarily elevating the eyebrow position and softening undesirable glabellar muscle activity to effect a more desirable appearance, comprising:
   injecting *botulinum* toxin (BTX) dissolved in microdroplets of injectable saline carrier to treat the septal and orbital orbicularis oculi muscles, on each side of a patient's face,
      wherein said *botulinum* toxin (BTX) comprises doses of 0.001 to 1.0 Unit equivalents of *Clostridum botulinum* toxin A;
      wherein said doses of BTX are dissolved in 0.01 to 0.05 ml microdroplets of injectable saline carrier;
      wherein said microdroplets of BTX solution are injected 0.5 to 1.0 millimeters below the skin surface where the muscles of facial expression responsible for eyebrow and glabellar depression insert into the skin;
      wherein said injected microdroplets of BTX are distributed over the muscles of facial expression responsible for eyebrow and glabellar depression including the septal and orbital orbicularis oculi muscles, and the inferior portion of the frontalis muscles where they insert into the skin at the level of the eyebrows;
      wherein the total number of microdroplets of *botulinum toxin* are adjusted to achieve the desired degree of muscle weakening.

2. The method of claim 1, further including the step of injecting *botulinum* toxin (BTX) dissolved in microdroplets of injectable saline carrier to treat the depressor supercilii muscle, on each side of the face,
   wherein said BTX comprises doses of 0.001 to 1.0 Unit equivalents of *botulinum* toxin A and dissolved in 0.01 to 0.05 ml of injectable saline carrier, and that is injected 0.5 to 1.0 millimeters below the skin surface just over the skin insertion of the depressor supercilii muscle on each side;
   wherein the total number of microdroplets of BTX is adjusted to achieve the desired degree of muscle weakening resulting in isolated treatment of the depressor supercilii muscles.

3. The method of claim 1, further including the step of injecting BTX dissolved in microdroplets to treat the procerus muscle,
   wherein said BTX comprises doses of 0.001 to 1.0 Unit equivalents of *botulinum* toxin A and dissolved in 0.01 to 0.05 ml of injectable saline carrier, and that is injected 0.5 to 1.0 millimeters below the skin surface just over the skin insertion of the procerus muscle;
   wherein the total number of microdroplets of BTX is adjusted to achieve the desired degree of muscle weakening resulting in isolated treatment of the procerus muscle.

4. The method of claim 1, further including the step of injecting *botulinum* toxin dissolved in microdroplets of injectable saline carrier to treat the corrugator supercilii muscle, on each side of the face, wherein said BTX comprises doses of 0.001 to 1.0 Unit equivalents of *botulinum* toxin A and dissolved in 0.01 to 0.05 ml of injectable saline carrier, and that is injected 0.5 to 1.0 millimeters below the skin surface just over the skin insertion of the corrugator supercilii muscle on each side;

wherein the total number of microdroplets of BTX is adjusted to achieve the desired degree of muscle weakening resulting in isolated treatment of the corrugator supercilii muscles.

5. The method of claim 1, further including the step of injecting *botulinum* toxin (BTX) comprising doses of 0.001 to 1.0 Unit equivalents of *botulinum* toxin A dissolved in 0.01 to 0.05 ml of injectable saline carrier, and that is injected 0.5 to 1.0 millimeters below the skin surface just over the skin insertion of the inferior limit of the frontalis muscle where it meets the superior aspect of the orbital portion of the orbicularis oculi muscle on each side;

wherein the total number of microdroplets of *botulinum* toxin is adjusted to achieve the desired degree of muscle weakening resulting in isolated treatment of the inferior limit of the frontalis muscle where it meets the superior aspect of the orbital portion of the orbicularis oculi muscle on each side.

6. The method of claim 1, further including the steps of injecting BTX comprising doses of 0.001 to 1.0 Unit equivalents of *botulinum* toxin A dissolved in 0.01 to 0.05 ml of injectable saline carrier, and that is injected 0.5 to 1.0 millimeters below the skin surface just over the skin insertion the muscles of facial expression;

wherein these muscles of facial expression include:

a. the inferior aspect of the frontalis muscle as it inserts into the orbital orbicularis oculi muscle and skin at the level of the eyebrow on each side;

b. the orbital and septal portions of the orbicularis oculi muscles on each side;

c. the depressor supercilli muscle on each side;

d. the procerus muscle;

e. the corrugator supercilli muscle on each side; and wherein the total number of microdroplets of *botulinum* toxin are adjusted to achieve the desired degree of muscle weakening.

7. The method of claim 1 wherein the *botulinum* toxin (BTX) is selected from the group consisting of *botulinum* toxin types A, B, C, D, E, F, and G as produced by the *Clostridium botulinum* bacterium; and wherein the concentration of the BTX solution prepared for microdroplet administration is adjusted based on the relative strength of the BTX product.

8. The method of claim 1, wherein the BTX is *botulinum* toxin A (BTX-A).

9. The method of claim 1 wherein the concentration of the BTX solution prepared for microdroplet administration is adjusted based on the relative strength of the BTX product used and the desired degree of muscle weakening.

10. The method of claim 1 wherein each microdroplet contains 0.25 to 0.5 Units of BTX-A.

11. The method of claim 1 wherein 30 to 100 microdroplet injections are distributed over the muscle groups to be treated.

12. The method of claim 1 wherein the distribution of the microdroplet injections are adjusted to enhance brow shape and symmetry.

\* \* \* \* \*